(12) United States Patent
Danti et al.

(10) Patent No.: US 10,314,943 B2
(45) Date of Patent: Jun. 11, 2019

(54) APPARATUS AND PROCESS FOR THE PREPARATION OF A BIOMIMETIC TISSUE PROSTHESIS OF THE TYMPANIC MEMBRANE

(71) Applicant: AZIENDA OSPEDALIERO-UNIVERSITARIA PISANA, Pisa (IT)

(72) Inventors: Serena Danti, Pistoia (IT); Stefano Berrettini, Lucca (IT); Stefano Marrazza, Pistoia (IT); Cesare Stefanini, Vicopisano (IT)

(73) Assignee: Azienda Ospedaliero-Universitaria Pisana, Pisa (IT)

( * ) Notice: Subject to any disclaimer, the term of this patent is extended or adjusted under 35 U.S.C. 154(b) by 302 days.

(21) Appl. No.: 15/023,335

(22) PCT Filed: Sep. 17, 2014

(86) PCT No.: PCT/IB2014/064593
§ 371 (c)(1),
(2) Date: Mar. 18, 2016

(87) PCT Pub. No.: WO2015/040554
PCT Pub. Date: Mar. 26, 2015

(65) Prior Publication Data
US 2016/0228606 A1    Aug. 11, 2016

(30) Foreign Application Priority Data

Sep. 20, 2013   (IT) .................. FI2013A0220

(51) Int. Cl.
*C12M 1/42* (2006.01)
*C12M 3/00* (2006.01)
(Continued)

(52) U.S. Cl.
CPC ....... *A61L 27/3645* (2013.01); *A61L 27/3604* (2013.01); *A61L 27/58* (2013.01);
(Continued)

(58) Field of Classification Search
CPC ..................... A61F 2240/001; C12M 21/08
(Continued)

(56) References Cited

U.S. PATENT DOCUMENTS

2013/0344531 A1* 12/2013 Akra ................ C12M 29/10
                                                          435/29
2014/0038258 A1*  2/2014 Akra ................ C12M 21/08
                                                          435/173.8

FOREIGN PATENT DOCUMENTS

JP          2007-185107      *  7/2007  ............ C12N 5/06

OTHER PUBLICATIONS

Machine translation of document No. JP 2007-185107 provided by JPO (translation of Figures provided by USPTO), Takezawa, 2007 (Year: 2007).*

(Continued)

*Primary Examiner* — Kevin Joyner
*Assistant Examiner* — Holly M Mull
(74) *Attorney, Agent, or Firm* — Duane Morris LLP

(57) ABSTRACT

The present invention refers to a process, and to the related apparatus, for the in vitro preparation of a biomimetic tissue prostheses of the tympanic membrane from mesenchymal stem cells; such prostheses are used for repairing or reconstructing the injured tympanic membrane in patients needing it, for example as a consequence of various trauma or pathologies.

10 Claims, 4 Drawing Sheets

(51) Int. Cl.
   *C12N 5/0775* (2010.01)
   *A61L 27/36* (2006.01)
   *A61L 27/58* (2006.01)
   *A61F 2/18* (2006.01)

(52) U.S. Cl.
   CPC ............ *C12M 21/08* (2013.01); *C12M 35/06* (2013.01); *C12N 5/0663* (2013.01); *A61F 2002/183* (2013.01); *A61F 2240/001* (2013.01); *A61L 2430/14* (2013.01); *C12N 2500/38* (2013.01); *C12N 2501/15* (2013.01); *C12N 2521/00* (2013.01); *C12N 2533/18* (2013.01); *C12N 2533/30* (2013.01)

(58) Field of Classification Search
   USPC ...................................................... 435/289.1
   See application file for complete search history.

(56) References Cited

OTHER PUBLICATIONS

International Search Report for International Application No. PCT/IB2014/064593, dated Dec. 17, 2014.
Written Opinion of the International Search Authority for Application No. PCT/IB2014/064593, dated Dec. 17, 2014.
International Preliminary Report on Patentability for Application No. PCT/IB2014/064593, dated Apr. 28, 2015.
Gooch, K. J. et al: "IFG-I and mechanical environment interact to modulate engineered cartilage development", Biochemical and Biophysical Research Communications, vol. 286, No. 5, Sep. 2001, pp. 909-915, XP002725821, ISSN: 0006-291X.
Hott, Morgan E. et al: "Fabrication of Tissue Engineered Tympanic Membrane Patches Using Computer-Aided Design and Injection Molding", The Laryngoscope, Willy-Blackwell, United States, vol. 114, No. 7, Jul. 2004, pp. 1290-1295, XP008103729, ISSN: 0023-852X, DOI: 10. 1097/0000537-200407000-00028 [retrived on Jan. 3, 2009].
Janjanin, S. et al: "Mold-Shaped, Nanofiber Scaffold-Based Cartilage Engineering Using Human Mesenchymal Stem Cells and Bioreactor", Journal of Surgical Research, Academic Press Inc., San Diego, CA, US vol. 149, No. 1, Sep. 2008, pp. 47-56, XP023905483, ISSN: 0022-4804, DOI: 10.1016/j.J.JSS. 2007. 12. 788 [Retrieved on Jan. 28, 2008].
Anisur, Rahman et al: "Stem cells and enhanced healing of chronic tympanic membrane perforation", ACTA Oto-Laryngologica, Apr. 2008, pp. 352-359, XP009178497, ISSN: 0001-6489.
Mei, Ting Bing et al: "Tissue Engineering of the Tympanic Membrane", Tissue Engineering Part B-Reviews, vol. 19, No. 2, Apr. 2013, pp. 116-132, XP002725820, p. 126, table 1A.

\* cited by examiner

APPARATUS AND PROCESS FOR THE PREPARATION OF A BIOMIMETIC TISSUE PROSTHESIS OF THE TYMPANIC MEMBRANE

FIELD OF THE INVENTION

The present invention concerns in general the field of medical biotechnologies, and more precisely it refers to an apparatus, and to the related process, for in vitro preparation of biomimetic tissue prostheses of the tympanic membrane, used for repairing or reconstructing the membrane itself in patients in needs thereof.

STATE OF THE ART

The tympanic membrane is unfortunately subject to various pathologies, which include in particular otitis media, tympanosclerosis, colesteatoma and perforation; the latter represents a very common clinical problem, especially in children, and it can be caused by many aetiological factors such as infection, trauma due to the entry of foreign bodies, insertion of surgical instruments in the external auditory canal, physical trauma or from deafening noise.

Although many perforations tend to heal spontaneously, chronic infections from perforations can lead to deafness, secondary infections, squamous epithelial cysts and formation of cholesteatoma (see for example Generi E. A. et al. *Ikiz. Otol. Neurotol.* 2003; 24: 371-6), events that require reconstructive surgery of the tympanic membrane, known as myringoplasty (M. Tos. *Manual of middle ear surgery*. Thieme Medical Publishers, Inc. New York 1993, vol. 1, Part II cap. 8-13).

The materials used up to now in such operations as replacements of the tympanic membrane, divided by type, are illustrated in the following table:

| | |
|---|---|
| Autologous | Temporal fascia, tragal perichondrium, fascia lata, periosteum, vein, fat, skin |
| Homologous | Tympanic membrane, dura mater |
| Heterologous | Bovine Peritoneum, bovine vein, porcine skin, porcine dura, collagen |
| Synthetic | Polyglactin, Gelfoam ®, polyvinyl alcohol, methyl-2-cyanoacrylate, polylactic acid, polyglycolic acid copolymers, polytetrafluoroethylene, bisphenol-A polycarbonate, copolymers of Polyactive ® |

Currently, the vein (only for small perforations), the perichondrium and the temporal fascia are the autologous materials most commonly used in myringoplasty. In particular, autograft of the temporal fascia is the most common method in surgical practice, with a success rate of closure of the perforation ranging from 88% to 95% (Rahman A. et al. *Acta Otolaryngol.* 2008 April; 128(4): 352-9; and Krause D. S. et al. *Cell* 2001; 105: 369-77). The temporal fascia up to now has been the most commonly used replacement material, and it undoubtedly constitutes the gold standard to which all other materials are currently compared, but it is not without drawbacks: the success rate is indeed nevertheless limited by the availability of the donor site and by the size of the lesion to be treated. Whereas small lesions can easily heal, the treatment of large perforations or of non-traumatic lesions through normal techniques, even with the materials that have given the best results, has often proven unsatisfactory and, especially for some patients, the risks and drawbacks of an operation are significant aspects that are not always acceptable. Moreover, in developing countries, the medical treatment of perforations of the tympanic membrane often is anyway not accessible.

Homologous transplants with tympanic membrane from a cadaver and with dura mater, on the other hand, have been rarely pursued due to the possible transmission of infective diseases, just like heterologous transplants, both of these types of transplant also not being generally being wanted by the patient, as well as being subject to rejection. Finally, the synthetic biomaterials currently used also have drawbacks that have repercussions on the outcome of the intervention, and indeed they suffer from rapid degradation, and can often lead to fibrosis of the middle ear.

Therefore, currently the ideal replacement material to be transplanted during myringoplasty interventions has yet to be found found (Teh B M, Marano R J, Shen Y, Friedland P L, Dilley R J, Atlas M D. Tissue engineering of the tympanic membrane. *Tissue Eng Part B Rev.* 2013 April; 19(2):116-32). This material should indeed be reliable, ensure a high success rate of the transplant and allow a low morbidity of the donor site. It should also constitute a sort of support framework, through which the epidermal layer can proceed to close the defect. This means that such a support should be colonised by mesenchymal cells and undergo neo-vascularization until a condensation of fibrous elements has formed between the migrating epithelium and the mucosa of the middle ear that will adequately replace, both morphologically and functionally, the original damaged tympanic membrane.

Therefore, the development of a replacement material of autologous origin that does not have the drawbacks described above for known materials and that can be used with high guarantees of success in myringoplasty interventions is still an objective that needs to be achieved. Such an objective is particularly challenging not only due to the difficulties inherent to the procedures of engineering tissues in general, but also due to the very nature of the particular tissue in question, i.e. that of the tympanic membrane.

The tympanic membrane, which has the extremely important function of transmitting vibrations generated by sound waves from the outer ear to the inner ear, whilst extremely thin, has a very complex structure: it is made up of two parts, the pars flaccida and the pars tensa, each with a triple-layer structure, in which between two epithelial layers there is an intermediate layer of connective tissue formed by collagen fibrils, mainly of collagen type II, constituting fibres that form bundles arranged in a complex manner (Ross M. H. et al. Istologia, *Testo e atlante con elementi di Biologia cellulare and molecolare*, Ambrosiana Publishing House, 2010). In the pars tensa, which represents almost the entire surface of the tympanic membrane, it is possible to distinguish, based on their different arrangement, different systems of fibres: the system of radiated fibres, that of circular fibres, that of parabolic fibres and finally that of transversal fibres. Such a particular constitution of the pars tensa is of fundamental importance in the transmission of sound, and therefore in the functionality of the tympanic membrane, but the formation mechanisms of such a structure during the development of the ear have not yet been clarified and this of course makes it even more difficult to develop a replacement material of the tympanic membrane that can adequately reproduce its functions imitating its morphology.

SUMMARY OF THE INVENTION

Now the Applicant has developed an apparatus and a process for in vitro preparation of a biomimetic tissue replacement of the tympanic membrane that allow to prepare, starting from mesenchymal stem cells, a material provided with characteristics reproducing those of the native membrane, and in particular the characteristics of the intermediate connective layer of the pars tensa of the eardrum, which are of essential importance in its functionality. The material obtained with the present process, using an innovative apparatus as bioreactor for the culture of starting stem cells, has shown that it possesses characteristics of dimensions, composition and spatial orientation of the collagen fibrils that are totally analogous to those detected by the anatomical studies of the native tympanic membrane, thus being able to also maintain its functional characteristics for correct transmission of sound. The apparatus of the invention also allows, thanks to a particular system of magnets, a cellular culture to be moved inside a growth solution without a contact with the culture itself, but thanks to the coupling between an external transduction apparatus and a biocompatible internal structure in which the culture of the cells is carried out.

Therefore, subject of the invention is an apparatus for in vitro preparation of a tissue prosthesis for repairing or reconstructing the tympanic membrane, whose essential characteristics are defined in the first of the attached claims.

A process for in vitro preparation of the aforementioned prosthesis, whose essential characteristics are defined in claim 11 attached hereto, and the tissue prosthesis that can thus be obtained, represent further subjects of the invention.

Characteristics and advantages of the preparation process, of the apparatus and of the tissue prosthesis according to the present invention will become clearer from the following detailed description of an embodiment thereof given as a non-limiting example, also with reference to the attached figures.

DETAILED DESCRIPTION OF THE INVENTION

In the present invention the terms "static" and "dynamic" respectively mean the modes of culture of the cells in the absence and in the presence of mechanical stimuli, generated in particular thanks to the apparatus of the invention.

With reference to the attached figures, and in particular to FIGS. 1-4, an apparatus according to a preferred embodiment of the present invention comprises a tube 1, of almost cylindrical shape and of dimensions suitable for containing the materials used for the cellular culture according to the process of the invention, connected to a hollow column 3 that, with a particular system described hereafter in detail, applies certain mechanical stimuli to it to move the cellular cultures inside the tube itself.

Figure 1:
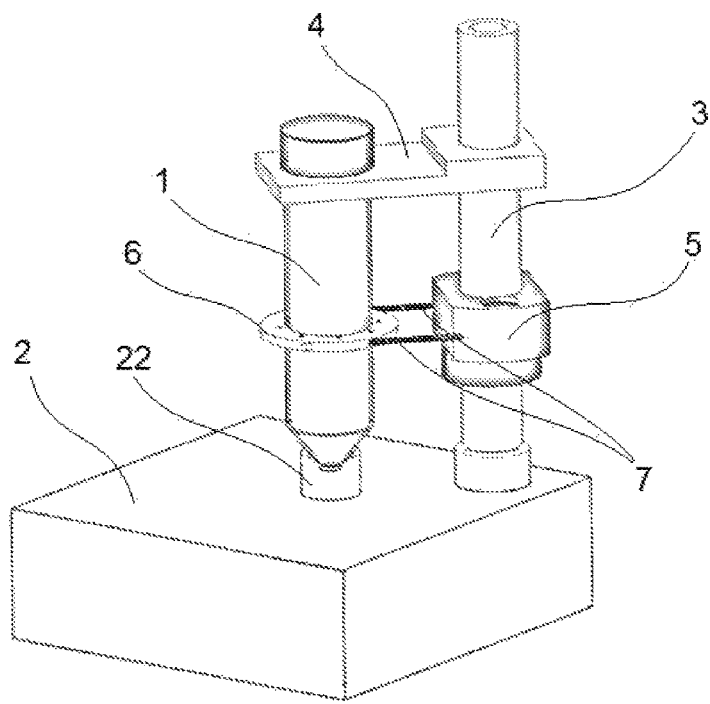
FIG. 1 is a perspective view of an embodiment of the apparatus of the invention.
Figure 2:
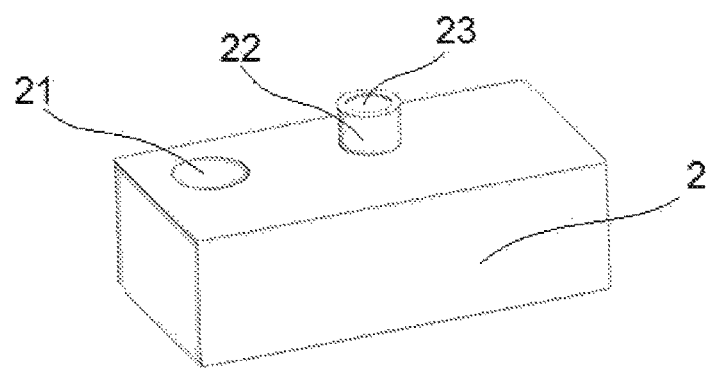
FIG. 2 is a perspective view of a base of the apparatus of FIG. 1.

With particular reference to FIGS. 1 and 2, the present apparatus comprises a base 2, provided with a hole 21 and with a stand 22 that elevates from the base 2 in a position adjacent to the hole 21, and is intended to support the tube 1 from below; its upper surface will therefore preferably be provided with a recess 23, of a shape suitable for housing the bottom of the tube 1. The hole 21 in the base 2, on the other hand, is intended to house the hollow column 3 in a position coaxial to the tube 1. In such a position, the column 3 and the tube 1 are also maintained thanks to a plate 4 provided with two holes suitable for housing tube 1 and column 3 through insertion of the plate from above, providing them with adequate stability during operation of the apparatus and allowing the tube to be easily extracted for the replacement of the cellular culture.

According to a preferred embodiment of the present invention, the tube 1 is to provided with a threading for closure from above with a screw cap, preferably knurled for better gripping by an operator and easy removal of the cap for the filling and emptying operations of the tube.

Inside the hollow column 3 there are magnetic means and a motor that moves the magnet alternately upwards and downwards, for a predetermined distance and time, while there is a cursor 5 anchored outside of the same hollow column 3, said cursor 5 being provided with magnetic means that, by interacting with the magnetic means inside the column, move the cursor 5 with motion that is guided by the inner magnetic means. The cursor 5, anchored to the column 3 and free to slide on it, is in turn also connected to a ring 6 that goes around the tube 1, through two rigid rods 7, preferably made from carbon, which transmit the movement of the cursor 5 to the ring 6, free to slide upwards and downwards on the walls of the tube 1. The motor in the hollow column 3 is for example a stepper motor, connected to a guide screw, which generates a vertical movement, transmitted inside the tube 1 thanks to the system of magnets.

The ring 6, provided with magnetic means, indeed constitutes an embodiment of an outer component of a system of magnetic rings that allow movements, and therefore mechanical stimuli, to be imparted to the cellular culture arranged inside the tube 1. The cells to be subjected to culture in the apparatus of the invention, suitably seeded on a suitable support in the form of a thin film, as described better hereafter, are indeed arranged between two rings 8a and 8b that keep the support film, and with it the cells, blocked before being inserted inside the tube 1; such rings 8a and 8b are of a diameter such as to be able to be inserted in the tube 1 so that their plane is arranged perpendicular to the longitudinal axis of the tube 1, and are provided with magnetic means; thanks to the presence of these magnetic means, they interact with the outer ring 6, and they undergo its movements accompanying the support with the cells in movement.

Figure 3:
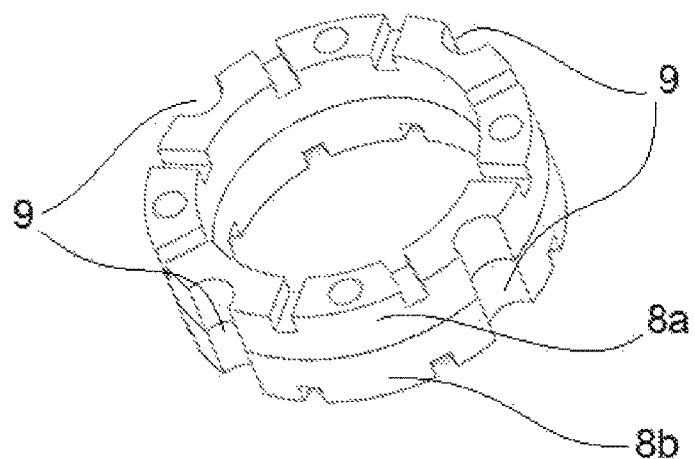
FIG. 3 shows a preferred embodiment of magnetic rings that are a component of the apparatus of FIG. 1.
Figure 4:
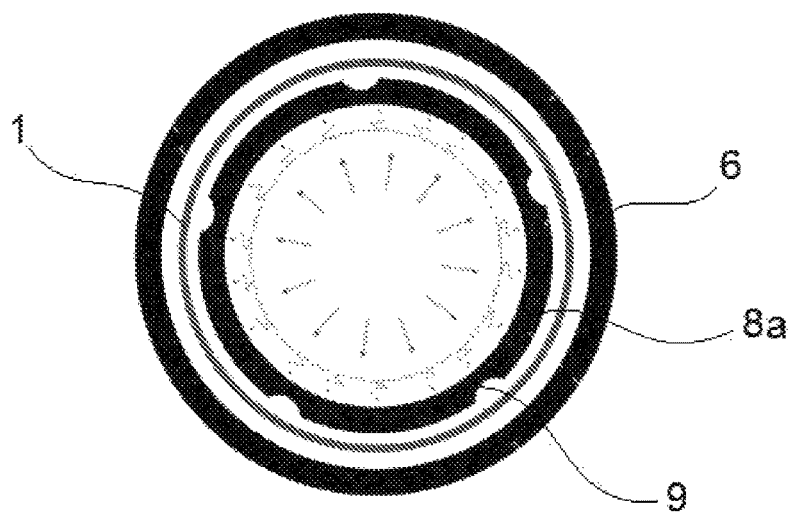
FIG. 4 shows a cross-section of a tube in the apparatus of FIG. 1 at the support of the growing cells.

FIG. 3 illustrates a preferred embodiment of the rings with inner magnetic means 8a and 8b, in which such rings are provided with grooves 9 along the outer perimeter intended to come into contact with the inner walls of the tube 1; such grooves 9 are arranged in line with each other in the two rings, so as to create a space that places in fluid communication the two parts into which the tube 1 is divided by the presence of the support with the cells, forcing the solution containing the growth medium present in the tube to pass from one side of the support to the other, with a radial motion tangential to the support surface, which goes from the centre to the periphery (FIG. 4), as a function of the support porosity, thus facilitating the movement of the support upwards and downwards in the solution and maintaining the same concentration of a growth medium for the cells on both sides of the support. FIG. 4 shows the cross section of a tube 1 at the support for the cells, in which it is possible to see the outer ring 6 going around the wall of the tube 1 and, inside it, one of the two inner rings 8a provided with grooves that keeps the support with the cells in position, indeed inserted between the two rings 8a and 8b. The closure of the support between the two rings 8a and 8b is carried out thanks to the magnets present on the rings themselves.

A magnetic force is transmitted to the support with the cells inside the tube by an external motor, which is in the hollow column in the particular embodiment illustrated in the attached figures, with a transmission of the motion that is contactless. Any kind of external motor able, via a magnetic force, to engage and drag the support with the cellular culture across the tube 1 in a contactless way, is suitable to carry out the present invention. The movement thus transmitted to the magnetic rings 8a and 8b inside the tube 1 moves the support with the cells move as a unit with such rings inside the solution of the growth medium that, thanks to the grooves 9, can slide in the space that is created between the outer perimeter of the rings 8a and 8b and the inner walls of the tube 1. The upward and downward movement of the rings creates substantially two types of tensions on the support of the cells, schematically illustrated with arrows in FIG. 4: an induced pressure, greater at the centre of the support, and a hydrodynamic shear stress, greater towards the periphery of the support; the movement transmitted to the support of the cells therefore provides two degrees of freedom for the production of different growth conditions in the cellular culture inside the apparatus of the invention. The control of such different growth conditions of the cells can be carried out both by acting on the speed and on the amplitude of the movement generated by the motor, and on the choice of the support of the cells, as described in detail hereafter.

The periodic vertical motion applied by the present bioreactor on the cellular construct inside the culture medium can be adjusted in the speed values for example from almost static to about 2.5 cm/s, preferably from about 1.5 to about 2.0 cm/s, by adjusting the amplitude of the periodic motion and its frequency. The amplitude of the motion will be set by the dimensions of the tube 1, and it can also be adjusted as a function of the amount of liquid culture medium used inside the tube itself; the amplitude of the motion can for example be comprised between about 3 and 10 cm, preferably between about 4 and 8 cm. As an example, lower amplitudes of the motion in the above said ranges result in lower stresses and are particularly preferred for co-culture of the tympanic membrane construct with epithelial cells (e.g. tympanic keratinocytes), while higher amplitudes resulting in stresses are mostly preferred for co-culture with endothelial cells (e.g. for neovascularization).

The base 2 of the present support, having a substantially parallelepiped shape, can act, in addition to as a support for tube and column with the motor, also for housing the electronic components necessary to drive the motor and impart the desired speed values and the direction of motion on the magnetic means inside the column 3. Advantageously, an on/off switch and a knob for adjusting the speed (not shown in the figures) can be arranged in an appropriate position on the base 2, so that the dynamic cellular growth conditions according to the invention can be easily modified and controlled by a user by simply actuating a knob.

The present apparatus, thanks to the presence of the magnetic means, that are preferably permanent magnets, has no external cables, and this makes it particularly suitable for use in humid environments, as well as allowing the necessary washing and sterilization operations before and after each cellular growth cycle.

Designs and materials with which the present apparatus can be made must be selected as a function of their use, which foresees many hours of continuous operation in a sterile environment, with a high humidity level and at higher temperatures than room temperature. The material preferably used to make the various parts of the apparatus is Teflon®, but the scope of the invention should also be considered to include any other equivalent material, which can easily be washed and sterilized, capable of withstanding the operative conditions to which the apparatus is subjected during normal operation; the parts of the apparatus are then connected together typically by stainless steel screws. The magnets to be subjected to sterilization according to the present invention are preferably selected among magnets having a Curie temperature higher than the sterilizing temperature in an autoclave.

According to a particular embodiment of the present apparatus, it will also comprise a pH sensor and a temperature sensor for detecting such parameters in order to evaluate their influence on the growth dynamics of the cellular culture, and consequently be able to modify and control such parameters to direct the cellular growth in the desired direction. The present apparatus may also comprise a suitable analyser for measuring the metabolite concentration in the cellular culture.

As shown in the following experimental part, the tensions-deformations produced by the apparatus of the invention on the support of the cells represent mechanical stimuli that contribute to differentiating the starting stem cells into fibroblasts of the tympanic membrane through the production of collagen of type II at the same time maintaining a fibroblast phenotype (non-chondrocytic). The Applicant has also demonstrated that such mechanical stimuli guide the organisation of the collagen fibres on the support towards a radial and circumferential arrangement of the fibres, going to emulate the same organisation of the fibres observed in the native tympanic membrane. The differentiation of the starting stem cells into fibroblasts can be further helped through chemical stimuli, i.e. through the use of a suitable culture medium with differentiating action.

According to a preferred embodiment of the present process, therefore, before introducing the support with the cells inside the present apparatus to move the culture, the support onto which the cells have been seeded are added to with a differentiating culture medium capable of promoting the chondrogenesis of the stem cells. A suitable differentiating culture medium according to the invention comprises, besides Foetal Bovine Serum (FBS), at least one differentiating agent in the chondrogenic sense, like for example TGF-beta (Transforming Growth Factor beta), ascorbic acid, BMPs (Bone Morphogenetic Proteins), b-FGF (basic Fibroblast Growth Factor), insulin-like growth factor, and similar; and preferably it comprises mixtures thereof. In the present differentiating culture medium the aforementioned agents can possibly be combined with one or more from sodium pyruvate, insulin-transferrin-selenium (ITS), L-glutamine, penicillin, streptomycin, linoleic acid, nutrient mixture F-12/D-MEM (Dulbecco's Modified Eagle Medium), and similar. Alternatively, it is possible to use chondrogenic differentiating culture mediums available on the market ready to use, like for example Miltenyi Biotec's ChondroDiff medium, which is optimised through addition of FBS.

Alternatively, the support on which the cells are seeded, before being introduced into the apparatus of the invention, can be added to with a suitable non-differentiating culture medium, like for example any suitable base culture medium, like D-MEM or alpha-MEM (alpha Modified Eagle Medium) with bovine foetal serum.

The support for the cells in the process according to the present invention must be in a material that is preferably biologically degradable and resorbable in longer time periods with respect to those necessary for the development of the prosthesis. This ensures that the cellular construct is completely developed before a full degradation of the biomaterial occurs: times of resorption of approximately 3 months or higher are considered optimal times, as they ensure full development and in vivo integration of the construct, although in vivo degradation times may strongly depend on the presence of active pathologies in the middle ear (Beutner D, Hüttenbrink K B. Passive and active middle ear implants. *Laryngorhinootologie* 2009 May; 88 Suppl 1:S32-47). The support must also have a porosity such as to facilitate the phenomena of agglomeration of the cells and prevent them from being carried away through the pores by the flow of growth liquid during the culture phase in the present apparatus; the pores of the material of the support will therefore have a smaller diameter than the diameter of the starting mesenchymal stem cells. In order to be able to be suitably arranged between the two rings 8a and 8b inside the tube and closed between them with magnetic closure, remaining in position during the dynamic culture phase inside the present apparatus, the support according to the invention is preferably made from a material equipped with a certain degree of elasticity, and with a substantially two-dimensional shape, by "substantially two-dimensional" meaning of negligible thickness with respect to the other dimensions even if sufficient to hold the cells and indeed perform its support function until resorption after implanting; the present support therefore behaves like a temporary "template". The present support, moreover, is preferably made from a non-porous material or equipped with micro- or nano-pores, in which case, however, the material has a hydrophobic nature, so as to limit the phenomena of transversal flow of the culture medium in the present apparatus; in other words, this type of support ensures that the flow that passes through the support itself is reduced or entirely absent with respect to the flow that passes through the grooves 9 between the inner walls of the tube 1 and the coupled rings 8a and 8b.

Materials for possible use for making a support are selected according to the invention among polymers of synthetic origin, natural polymers or mixtures thereof (for example bio-artificial polymers) able to be processed in the form of substantially two-dimensional supports, both in the form of dense supports (for example in the form of micro- or nano-films) and in the form of tissues of tightly meshed micro- or nano-fibres (for example in the form of electrospun tissues). Hereafter are listed the numerous classes of synthetic and/or natural polymers, which are hydrolithically and/or enzymatically degradable, and suitable for biomedical use, which can be processed according to the requirements illustrated above. Synthetic polymers that can possibly be used according to the invention are selected among polyanhydrides, polycarbonates, polyalphaesters, polyesters, polyurethanes, polyorthoesters, polyacetals, polyphosphazenes, polyamides, and copolymers or mixtures thereof. Among polyalphaesters, preferably use is made of polylactides, for example polylactic acid, polyglycolides, for example polyglycolic acid, and polycaprolactones, for example poly(ε-caprolactone) indicated here as PCL, both linear and in star-form, indicated here as *PCL. That which is particularly preferred for making the present invention is star-shaped poly(ε-caprolactone) (*PCL).

According to a particular embodiment of the present invention the aforementioned polymers can be doped with nanoparticles, for example nano-spheres, nanotubes, and similar, to promote the chondrogenic-like differentiation and/or to modulate the chemical-physical, surface or structural properties of the base polymer like for example hydrophobicity, roughness, elastic modulus etc.; examples of nanoparticles that can possibly be used are hydroxyapatite nanoparticles (HA) (Spadaccio et al., *Ann Biomed Eng.* 2009 July, 37:1376-1389), drug-release nanoparticles, and the like.

Polymers of natural origin that can possibly be used according to the invention can be selected among polysaccharides, for example derivatives of cellulose, of chitin, of hyaluronic acid and similar, and proteins, like for example polymers of fibronectin, like fibrinogen, collagens and elastin.

According to a particularly preferred embodiment of the invention the support is made in star-shaped poly(ε-caprolactone) (*PCL), possibly doped with hydroxyapatite nanoparticles (*PCL/HA), in the form of non-woven fabric of microfibers obtained by electrospinning.

According to a particular embodiment of the invention, the support is provided with topographical patterns (micropatterns) on the surface on which the cells are seeded, which create paths capable of guiding the arrangement of the seeded stem cells and the subsequent production of collagen along the directions indicated by the patterns themselves. In this way, it is possible to facilitate the formation of agglomerates of collagen along the desired directions, which are those observed in the native tympanic membrane, creating topographical stimuli for the cells on the surface of the support. For these reasons the use of topographical patterns is preferred according to the invention, even if the desired tissue prostheses of the tympanic membrane can be obtained by means of the present apparatus and preparation process without using the above said topographical patterns the cellular culture and the production of collagen being guided by continuous motion imposed by the present apparatus.

Experimental Part

In the following experiments human mesenchymal stem cells were used, isolated from the bone marrow of patients undergoing hip replacement surgery at the azienda Ospedaliero-Universitaria Pisana, Hematology Research Unit, in Pisa. The patients gave their written consent, of free will and fully informed, for the harvesting and study carried out on the cellular material harvested, and described hereafter.

Cultures of the Cells and Analysis of the Cellular Vitality and Spatial Orientation in the Samples Obtained The mesenchymal stem cells were isolated through centrifuging by density gradient (Ficoll Histopaque), according to standard protocols, and expanded in Dulbecco's Modified Eagle Medium (D-MEM) added with 10% bovine foetal serum (FBS; Invitrogen, USA), L-Glutamine 200 mM (Invitrogen), 100 U/mL of penicillin and 0.1 mg/mL of streptomycin (Lonza) and kept in an incubator at 37° C. with humidified atmosphere and 5% $CO_2$.

The cells thus isolated were seeded on supports in non-woven fabric based on microfibres of star-shaped poly(ε-caprolactone), as such or doped with hydroxyapatite nanoparticles (*PCL and *PCL/HA, respectively), obtained by electrospinning. Such supports were seeded with 250,000 mesenchymal stem cells per support, again using the aforementioned culture medium used for the expansion of the cells as culture medium.

After 72 hours from seeding of the cells on the supports, part of the cell/support constructs of *PCL or of *PCL/HA thus obtained was added with a differentiating medium consisting of D-MEM:F-12 Nutrient Mixture (Sigma-Aldrich) added with 10 ng/ml of TGF-β1 (Peprotech), 50 ng/ml of ascorbic acid (Sigma), 10% FBS (Invitrogen), L-Glutamine 200 mM (Invitrogen), 100 U/mL of penicillin and 0.1 mg/mL of streptomycin (Lonza). A part of the cell/support constructs of *PCL was, on the other hand, kept in the non-differentiating medium, cultivating the cells for a further 36 hours so as to facilitate its adhesion to the substrate.

All of the constructs thus prepared were subjected to a further culture phase of the cells for 7 days in static and in dynamic conditions, i.e. in a bioreactor of the invention in which the amplitude of the periodic motion imposed on the support was regulated at 4.55 cm and its frequency at 0.2 Hz, thus resulting in an average speed of 1.82 cm/s.

Figure 5:
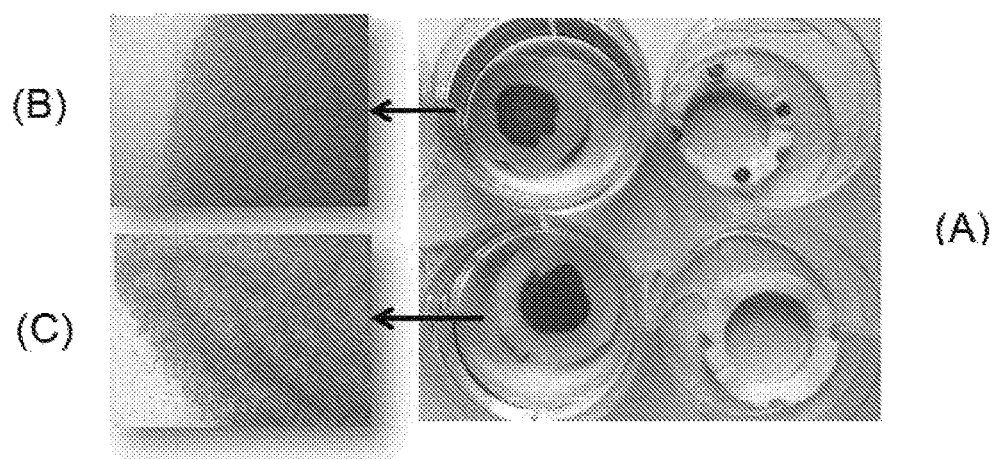
FIG. 5 shows the natural size photographs (A) and the micrographs taken with a stereomicroscope of the two samples obtained from cell cultures with differentiating medium in static conditions (B) and dynamic conditions using the present apparatus (C)
Figure 6:
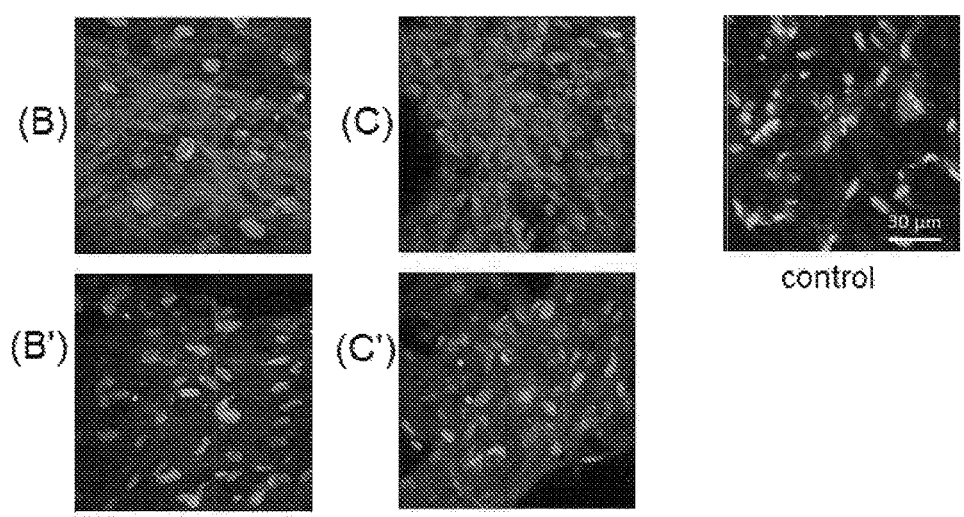
FIG. 6 shows the confocal microscope images obtained for the two samples (B) and (C) of FIG. 5; and for two other samples obtained under the same culture conditions, but on a support in star branched poly(ε-caprolactone) added with hydroxyapatite nanoparticles *PCL/HA instead of on a support of star branched poly(ε-caprolactone) *PCL.

The material thus obtained was finally subjected to the Neutral Red test that, dyeing the vital cells red, allows them to be spatially located. The results of the test showed, both for the samples from static culture and for the samples cultivated in the bioreactor of the invention, a substantial area of the cell-covered surface, of comparable dimensions to the native tympanic membrane. In FIG. 5 it is possible to see, for example, the results of the test obtained for cells seeded on *PCL, and cultivated in static and dynamic conditions in non-differentiating medium; in particular the photographs at natural size (A) and with stereomicroscopy of the two samples in static conditions (B) and in dynamic conditions (C) are shown. From these results it has been possible to note how, whereas the static culture created a homogeneous distribution of the cells [image (B)], in the case of the dynamic culture in the apparatus of the invention it is possible to observe a phenomenon of agglomeration of the cells according to semi-circular lines [image (C)]. In the same images it is possible to see the clear edge, and therefore the absence of cells in this area, due to the presence of the supporting frame of the support, present in both of the samples and useful for the surgical coupling of the material obtained with the surrounding areas. FIGS. 6 (B) and (C), on the other hand, shows the confocal microscope images obtained for two samples analogous samples to those of FIG. 5, but obtained using differentiating medium, and FIGS. 6 (B') and (C') shows the images obtained for two samples that have been subjected to the same culture conditions, but with support in *PCL/HA instead of in *PCL. It should be noted that in green, with an oval shape, there are the nuclei of the cells, and the filaments of F-actin are marked in red. Such images confirm, at a microscopic level, what has already been shown by the previous images, i.e. that the use of the present apparatus as bioreactor for the culture of cells, as well as substantially maintaining or even increasing the good cellular vitality already shown by the samples cultivated in static conditions, also creates a particular orientation of the cells that emulates that of the pars tensa of the native membrane. In FIG. 6 it is also possible to see the image obtained for a control sample made by seeding the cells on a support in *PCL, without differentiating medium and in static culture conditions, from which it can clearly be seen how the cellular vitality is in this case much lower.

Histological Analysis of the Samples

In order to determine the composition and the characteristics of the material obtained to evaluate its affinity with the native tympanic membrane, identification was made of the markers considered to be significant, i.e. collagens I, II, III and IV, and the anti-fibroblast antibody, going to detect its expression in the different culture conditions of the cells. The following Table 1 shows the scores for the intensity of the antigen, determined by observation by microscope, according to the following criteria:

"−" is negative
"+" is slightly positive
"++" is positive
"+++" is strongly positive
"++++" is very strongly positive

TABLE 1

|  | *PCL non-differentiated static | *PCL differentiated static | *PCL differentiated dynamic | *PCL-HA differentiated static | *PCL-HA differentiated dynamic |
|---|---|---|---|---|---|
| anti-fibroblast | ++ | +++ | ++++ | ++ | ++++ |
| intracellular anti-collagen I | + | +++ | ++/+++ | +++ | ++ |
| extracellular anti-collagen I | − | +/− | +/− | +/− | +/− |
| anti-collagen II | + | + | ++ | + | + |
| anti-collagen III | +/− | + | + | + | + |
| anti-collagen IV | + | ++ | + | +/− | + |

From the results obtained it emerges how the surface antigen typical of fibroblasts is expressed in all of the samples, however with an increase in the differentiated samples and with a further increase of the expression in the samples also subjected to mechanical stimuli in the apparatus of the invention. A similar pattern can be observed for collagen I at intracellular level, which has a low expression in the non-differentiated sample, increasing in the differentiated samples, with a prevalently intracellular cytoplasmatic positivity. The expression of collagen II is weak and, although present in all of the samples, increasing in the differentiated sample cultivated in the apparatus of the invention, in particular in the sample with the support in *PCL.

Figure 7:
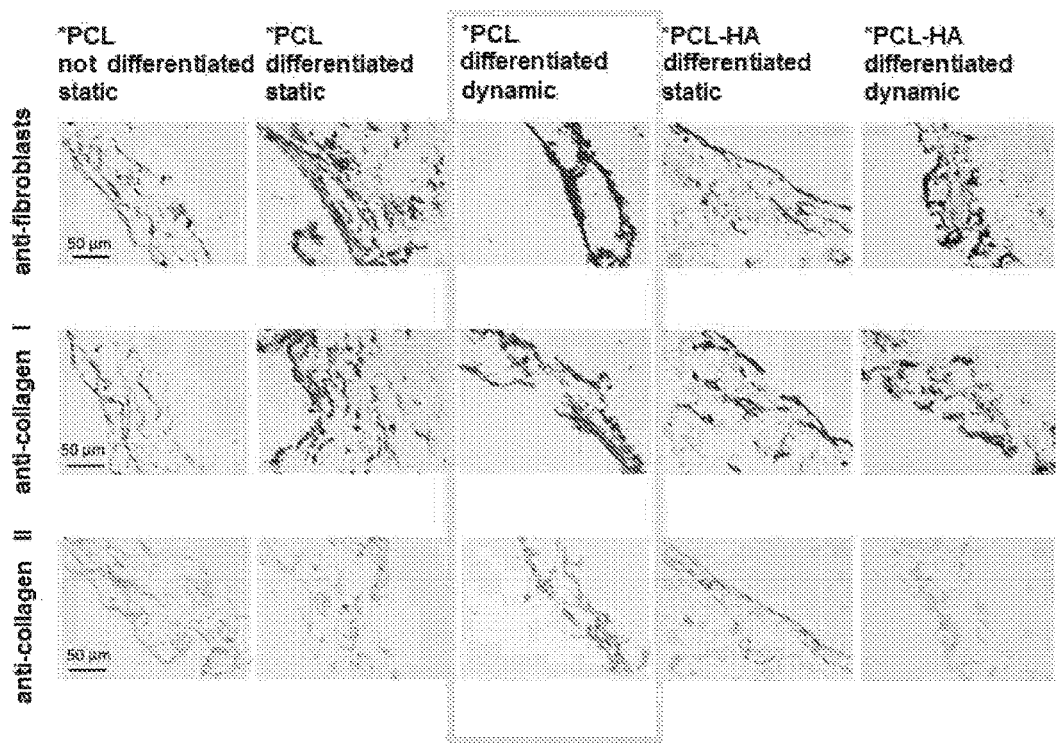
FIG. 7 shows, for the different samples analysed, the images obtained by the immunohistochemical analysis relative to the expression of the fibroblast antigen and of collagens of type I and type II in the cellular constructs produced with the system subject of the invention (dynamic culture with differentiating medium) using supports in *PCL and in *PCL/HA, and the relative static controls and controls with non-differentiating medium.

FIG. 7 shows immunohistochemical images by optical microscope, representative of the samples analysed. Such images highlight how the antigens are expressed and where they are located (intra- or extra-cellular) and their distribution in the cellular constructs analysed. Immunohistochemistry is a method that allows information to be obtained through the use of antigen-antibody reactions, then detected by a suitable chromogen. This method is based on the bond in sequence of a series of di molecules that connect the surface antigen to the chromogen substrate, at the same time amplifying the reaction to make it clearly visible by optical microscope, and in the present case it was carried out with the following procedure.

After elimination of the inclusion and rehydration medium, the sections underwent a suitable unmasking treatment to provide the antigens of interest for the bond with the primary antibodies. In most cases the permeabilization of the samples was carried out using 0.2% Triton X-100 (Sigma) for 10 min, whereas for the unmasking of the antigen Collagen II the sections were incubated in a citrate buffer (Diapath, Italia) placed in a thermostatted bath at 90° C. for 10 minutes. Thereafter, the sections were incubated in a methanol solution containing 0.6% 36-volume hydrogen peroxide to block the activity of the endogene peroxidase present ion the samples, washed in distilled water and PBS 1× and incubated with the serum of the animal species in which the secondary antibody was obtained, Goat Serum diluted 1:20 in PBS1× 20 minutes at 37° C., in order to block possible aspecific bonds of the secondary antibodies themselves. The sections were then incubated for one night at 4° C. with the primary antibody diluted in bovine serum albumin (BSA). The primary antibodies used were the following: polyclonal rabbit anti-collagen I antibody 1:1200 (ab34710, abCam, USA), monoclonal mouse anti-collagen II antibody 1:50 (sc52658, Santa Cruz), monoclonal mouse anti-Fibroblast 1:6000 antibody (Sigma). The negative controls were obtained by incubating some sections only with 0.1% di BSA. The day after, the sections were incubated with the secondary biotynilated antibodies for 1 hour at room temperature and then with peroxidated streptavidin (Vectastain Elite ABC Kit Standard, Vector Lab) for 30 minutes. The immunoreactivity was shown in brown by incubating the samples for 5 minutes in the dark with the chromogen substrate 3-3'-diaminobenzidine tetrahydrochloride (DAB) containing 0.02% hydrogen peroxide. Then there was counterstaining with haematoxylin for 30 seconds developed in running water for 1 minute to dye the nuclei. Finally, the sections were dehydrated, clarified and mounted in balsam. The dyes and the immunohistochemical reactions were observed and photographed by optical microscope.

The invention claimed is:

1. An apparatus for the in vitro preparation of a tissue prosthesis for repairing or reconstructing a tympanic membrane, comprising
    a tube in which a support for mesenchymal stem cells is placed having the edges blocked between two rings including a first ring and a second ring,
    said apparatus being characterized in that said two rings are provided with a first magnetic means suitable for interacting with a second external magnetic means so that such interaction determines: the anchoring of said two rings to the inner walls of said tube with the rings plane perpendicular to the longitudinal axis of the tube, and a continuous motion of said two rings, and consequently of said support, along said axis of the tube, alternately upwards and downwards, for a predetermined distance and time,
    said apparatus further comprising a third ring provided with said second magnetic means and surrounding said tube being free to slide over it, a hollow column comprising inside a motor means and a third magnetic means, and a cursor provided with a fourth magnetic means able to interact with said third magnetic means, connected to said third ring, anchored to said column and free to slide over it, said motor means being able to generate a continuous motion of said third magnetic means within said hollow column, and consequently of said cursor, of said ring and of said rings, alternatively upwards and downwards, for a predetermined distance and time.

2. The apparatus according to claim 1, wherein said two rings are provided with grooves that put in fluid communication two parts of said tube resulting from the presence of said support.

3. The apparatus according to claim 1, wherein said first magnetic means are also suitable for blocking, with magnetic closure, the edges of said support between said two rings and leaving uncovered the central portion of the support for cells seeding.

4. The apparatus according to claim 1, wherein said cursor and said third ring are connected between each other by means of two carbon rods.

5. The apparatus according to claim 1, further comprising a base provided with a hole and with a stand which elevates from said base in a position adjacent to said hole, said hole being suitable for housing said hollow column and said stand being suitable for supporting said tube so as to maintain said column and said tube in coaxial position at a distance which is equal to the length of said rods.

6. The apparatus according to claim 1, further comprising a plate provided with two adjacent holes suitable for housing respectively said tube and said hollow column thus proving them adequate stability during operation of the apparatus and allowing the tube to be easily extracted for replacement of the cellular culture.

7. The apparatus according to claim 1, wherein one of said first, second, third and fourth magnetic means is a permanent magnets.

8. The apparatus according to claim 1, further comprising a pH sensor and/or a temperature sensor and/or a suitable analyzer for respectively sensing and measuring pH and/or temperature and/or metabolite concentration inside said tube.

9. The apparatus according to claim 1, further comprising control means comprising electronic components connected with said motor means for regulating the speed and direction of motion of said third magnetic means.

10. The apparatus according to claim 1, wherein said first and second magnetic means are permanent magnets.

* * * * *